US012533222B2

(12) United States Patent
Krahbichler

(10) Patent No.: US 12,533,222 B2
(45) Date of Patent: Jan. 27, 2026

(54) DEVICE AND METHOD FOR DELIVERY OF MEDICAL DEVICES TO A CARDIAC VALVE

(71) Applicant: Emboline, Inc., Santa Cruz, CA (US)

(72) Inventor: Erik Krahbichler, Helsingborg (SE)

(73) Assignee: Emboline, Inc., Santa Cruz, CA (US)

( * ) Notice: Subject to any disclaimer, the term of this patent is extended or adjusted under 35 U.S.C. 154(b) by 377 days.

(21) Appl. No.: 17/820,131

(22) Filed: Aug. 16, 2022

(65) Prior Publication Data

US 2022/0387162 A1 Dec. 8, 2022

Related U.S. Application Data

(60) Division of application No. 16/560,194, filed on Sep. 4, 2019, now Pat. No. 11,992,398, which is a continuation of application No. 14/675,483, filed on Mar. 31, 2015, now Pat. No. 10,433,946, which is a continuation of application No. 14/115,088, filed as application No. PCT/EP2012/058384 on May 7, 2012, now Pat. No. 9,023,101.

(60) Provisional application No. 61/483,689, filed on May 8, 2011.

(30) Foreign Application Priority Data

May 8, 2011 (EP) .................................... 11165215

(51) Int. Cl.
*A61F 2/01* (2006.01)
*A61F 2/24* (2006.01)

(52) U.S. Cl.
CPC .............. *A61F 2/013* (2013.01); *A61F 2/014* (2020.05); *A61F 2/2427* (2013.01); *A61F 2/2433* (2013.01)

(58) Field of Classification Search
CPC ........ A61F 2/013; A61F 2/2427; A61F 2/243; A61F 2/2433; A61F 2/247
See application file for complete search history.

(56) References Cited

U.S. PATENT DOCUMENTS

| | | | |
|---|---|---|---|
| 4,850,358 | A | 7/1989 | Millar |
| 5,411,552 | A | 5/1995 | Anderson et al. |
| 5,468,225 | A | 11/1995 | Teirsein |

(Continued)

FOREIGN PATENT DOCUMENTS

| | | |
|---|---|---|
| JP | 2003517592 A | 5/2003 |
| JP | 2011525405 A | 9/2011 |

(Continued)

OTHER PUBLICATIONS

Reichenspurner et al.; Particulate emboli capture by an intra-aortic filter device during cardiac surgery; The Journal of Thoracic and Cardiovascular Surgery; 119(2); pp. 233-241; Feb. 1, 2000.

(Continued)

*Primary Examiner* — Dianne Dornbusch
(74) *Attorney, Agent, or Firm* — Shay Glenn LLP

(57) ABSTRACT

A catheter device for transvascular delivery of a medical device to a cardiac valve region of a patient comprises an elongate sheath with a first lumen, a distal end for positioning at a heart valve, a second lumen that extends parallel to or in the sheath, and an expandable embolic protection filter. The filter is arranged to extend from an orifice of the second lumen and, in the expanded, covers ostia of the side branch vessels in the aortic arch.

8 Claims, 12 Drawing Sheets

(56) References Cited

U.S. PATENT DOCUMENTS

| | | | |
|---|---|---|---|
| 5,584,803 | A * | 12/1996 | Stevens ................. A61F 2/2433 604/6.16 |
| 5,667,523 | A | 9/1997 | Bynon et al. |
| 5,678,570 | A | 10/1997 | Manning |
| 5,766,151 | A * | 6/1998 | Valley ............... A61M 39/0247 604/103.07 |
| 5,769,812 | A | 6/1998 | Stevens et al. |
| 5,769,816 | A | 6/1998 | Barbut et al. |
| 5,795,325 | A | 8/1998 | Valley et al. |
| 5,868,708 | A | 2/1999 | Hart et al. |
| 5,910,154 | A | 6/1999 | Tsugita et al. |
| 5,916,193 | A | 6/1999 | Stevens et al. |
| 5,957,949 | A | 9/1999 | Leonhardt et al. |
| 6,051,014 | A | 4/2000 | Jang |
| 6,117,064 | A | 9/2000 | Apple et al. |
| 6,139,517 | A | 10/2000 | Macoviak et al. |
| 6,142,987 | A | 11/2000 | Tsugita |
| 6,214,026 | B1 | 4/2001 | Lepak et al. |
| 6,235,044 | B1 | 5/2001 | Root et al. |
| 6,245,088 | B1 | 6/2001 | Lowery |
| 6,258,120 | B1 | 7/2001 | McKenzie et al. |
| 6,290,656 | B1 | 9/2001 | Boyle et al. |
| 6,348,063 | B1 | 2/2002 | Yassour et al. |
| 6,361,545 | B1 | 3/2002 | Macoviak et al. |
| 6,371,935 | B1 | 4/2002 | Macoviak et al. |
| 6,395,014 | B1 | 5/2002 | Macoviak et al. |
| 6,402,736 | B1 | 6/2002 | Brown et al. |
| 6,537,294 | B1 | 3/2003 | Boyle et al. |
| 6,547,760 | B1 * | 4/2003 | Samson ........... A61B 17/12045 604/101.01 |
| 6,585,715 | B1 | 7/2003 | Teirstein |
| 6,620,182 | B1 | 9/2003 | Khosravi et al. |
| 6,673,089 | B1 | 1/2004 | Yassour et al. |
| 6,689,150 | B1 | 2/2004 | Van Tassel et al. |
| 6,695,864 | B2 | 2/2004 | Macoviak et al. |
| 6,709,415 | B2 | 3/2004 | Navia et al. |
| 7,169,165 | B2 | 1/2007 | Belef et al. |
| 7,323,001 | B2 | 1/2008 | Clubb et al. |
| 7,371,250 | B2 | 5/2008 | Mazzocchi et al. |
| 7,637,920 | B2 | 12/2009 | von Lehe et al. |
| 7,651,514 | B2 | 1/2010 | Salahieh et al. |
| 7,749,245 | B2 | 7/2010 | Cohn et al. |
| 8,182,530 | B2 | 5/2012 | Huber |
| 8,221,445 | B2 | 7/2012 | Van Tassel et al. |
| 8,388,644 | B2 | 3/2013 | Parker |
| 8,512,398 | B2 | 8/2013 | Alkhatib |
| 8,663,319 | B2 | 3/2014 | Ho |
| 8,778,017 | B2 | 7/2014 | Eliasen et al. |
| 8,840,663 | B2 | 9/2014 | Salahieh et al. |
| 8,974,490 | B2 | 3/2015 | Jonsson |
| 9,023,101 | B2 | 5/2015 | Krahbichler |
| 9,579,182 | B2 | 2/2017 | Krahbichler |
| 9,968,359 | B2 | 5/2018 | Jonsson |
| 10,433,946 | B2 | 10/2019 | Krahbichler |
| 10,512,468 | B2 | 12/2019 | Jonsson |
| 10,568,736 | B2 | 2/2020 | Meiri et al. |
| 10,575,852 | B2 | 3/2020 | Jonsson |
| 11,278,388 | B2 | 3/2022 | Krahbichler |
| 11,446,132 | B2 | 9/2022 | Krahbichler |
| 11,957,561 | B2 | 4/2024 | Krahbichler |
| 2001/0044591 | A1 | 11/2001 | Stevens et al. |
| 2002/0002383 | A1 | 1/2002 | Sepetka et al. |
| 2002/0058995 | A1 | 5/2002 | Stevens |
| 2002/0077596 | A1 | 6/2002 | McKenzie et al. |
| 2002/0133115 | A1 | 9/2002 | Gordon et al. |
| 2002/0143362 | A1 | 10/2002 | Macoviak et al. |
| 2002/0161389 | A1 | 10/2002 | Boyle et al. |
| 2002/0169437 | A1 | 11/2002 | Macoviak et al. |
| 2003/0004539 | A1 | 1/2003 | Linder et al. |
| 2003/0040736 | A1 | 2/2003 | Stevens et al. |
| 2003/0078519 | A1 | 4/2003 | Salahieh et al. |
| 2003/0130680 | A1 | 7/2003 | Russell |
| 2003/0153942 | A1 | 8/2003 | Wang et al. |
| 2003/0153943 | A1 | 8/2003 | Michael et al. |
| 2003/0158574 | A1 | 8/2003 | Esch et al. |
| 2003/0171803 | A1 | 9/2003 | Shimon |
| 2003/0195609 | A1 | 10/2003 | Berenstein et al. |
| 2003/0199759 | A1 | 10/2003 | Richard |
| 2004/0073253 | A1 | 4/2004 | Morrill et al. |
| 2004/0215167 | A1 | 10/2004 | Belson |
| 2004/0225354 | A1 | 11/2004 | Allen et al. |
| 2005/0055047 | A1 | 3/2005 | Greenhalgh |
| 2005/0085842 | A1 | 4/2005 | Eversull et al. |
| 2005/0119688 | A1 | 6/2005 | Bergheim |
| 2005/0137689 | A1 | 6/2005 | Salahieh et al. |
| 2005/0137696 | A1 | 6/2005 | Salahieh et al. |
| 2005/0209582 | A1 | 9/2005 | Quinn et al. |
| 2005/0216031 | A1 | 9/2005 | White et al. |
| 2006/0015138 | A1 | 1/2006 | Gertner |
| 2006/0020285 | A1 | 1/2006 | Niermann |
| 2006/0025806 | A1 | 2/2006 | Krolik et al. |
| 2006/0074484 | A1 | 4/2006 | Huber |
| 2006/0074485 | A1 | 4/2006 | Realyvasquez |
| 2006/0161241 | A1 | 7/2006 | Barbut et al. |
| 2006/0241675 | A1 | 10/2006 | Johnson et al. |
| 2006/0253148 | A1 | 11/2006 | Leone et al. |
| 2006/0259066 | A1 | 11/2006 | Euteneuer |
| 2006/0287668 | A1 | 12/2006 | Fawzi et al. |
| 2007/0027534 | A1 | 2/2007 | Bergheim et al. |
| 2007/0088383 | A1 | 4/2007 | Pal et al. |
| 2007/0142906 | A1 | 6/2007 | Figulla et al. |
| 2007/0270901 | A1 | 11/2007 | Shimon et al. |
| 2008/0004688 | A1 | 1/2008 | Spenser et al. |
| 2008/0065145 | A1 | 3/2008 | Carpenter |
| 2008/0140110 | A1 | 6/2008 | Spence |
| 2008/0147111 | A1 | 6/2008 | Johnson et al. |
| 2008/0147160 | A1 | 6/2008 | Ghione et al. |
| 2008/0147181 | A1 | 6/2008 | Ghione et al. |
| 2008/0147182 | A1 | 6/2008 | Righini et al. |
| 2008/0269877 | A1 | 10/2008 | Jenson et al. |
| 2009/0030510 | A1 | 1/2009 | Ho |
| 2009/0062836 | A1 | 3/2009 | Kurrus |
| 2009/0254172 | A1 | 10/2009 | Grewe |
| 2009/0287182 | A1 | 11/2009 | Bishop et al. |
| 2009/0326575 | A1 | 12/2009 | Galdonik et al. |
| 2010/0076482 | A1 | 3/2010 | Shu et al. |
| 2010/0094209 | A1 | 4/2010 | Drasler et al. |
| 2010/0099946 | A1 | 4/2010 | Jenkins et al. |
| 2010/0179583 | A1 | 7/2010 | Carpenter et al. |
| 2010/0179584 | A1 | 7/2010 | Carpenter et al. |
| 2010/0191276 | A1 | 7/2010 | Lashinski |
| 2010/0211095 | A1 | 8/2010 | Carpenter |
| 2010/0228280 | A1 | 9/2010 | Groothuis et al. |
| 2010/0312268 | A1 | 12/2010 | Belson |
| 2010/0324589 | A1 | 12/2010 | Carpenter et al. |
| 2011/0027038 | A1 | 2/2011 | Hsu et al. |
| 2011/0040232 | A1 | 2/2011 | Magal |
| 2011/0172697 | A1 | 7/2011 | Jonsson |
| 2011/0270388 | A9 | 11/2011 | Stevens |
| 2011/0295304 | A1 | 12/2011 | Jönsson |
| 2012/0172915 | A1 | 7/2012 | Fifer et al. |
| 2013/0103075 | A1 | 4/2013 | Wang et al. |
| 2013/0123835 | A1 | 5/2013 | Anderson et al. |
| 2013/0184739 | A1 | 7/2013 | Brady et al. |
| 2013/0238010 | A1 | 9/2013 | Johnson et al. |
| 2013/0245669 | A1 | 9/2013 | Basu et al. |
| 2014/0074148 | A1 | 3/2014 | Glenn et al. |
| 2014/0074152 | A1 | 3/2014 | Shezifi et al. |
| 2015/0066075 | A1 | 3/2015 | Russell et al. |
| 2015/0313701 | A1 | 11/2015 | Krahbichler |
| 2020/0197016 | A1 | 6/2020 | Jonsson |
| 2022/0387161 | A1 | 12/2022 | Krahbichler |
| 2024/0173116 | A1 | 5/2024 | Jonsson |
| 2024/0245500 | A1 | 7/2024 | Krahbichler |
| 2024/0307167 | A1 | 9/2024 | Krahbichler |

FOREIGN PATENT DOCUMENTS

| | | | |
|---|---|---|---|
| WO | WO97/42878 | A1 | 11/1997 |
| WO | WO99/12478 | A1 | 3/1999 |
| WO | WO99/32050 | A1 | 7/1999 |
| WO | WO00/43062 | A1 | 7/2000 |
| WO | WO00/44313 | A1 | 8/2000 |
| WO | WO01/08743 | A1 | 2/2001 |

(56) References Cited

FOREIGN PATENT DOCUMENTS

| | | | |
|---|---|---|---|
| WO | WO01/35870 | A1 | 5/2001 |
| WO | WO01/56484 | A1 | 8/2001 |
| WO | WO02/056955 | A1 | 7/2002 |
| WO | WO03/047648 | A2 | 6/2003 |
| WO | WO03/105721 | A2 | 12/2003 |
| WO | WO2004/006803 | A1 | 1/2004 |
| WO | WO2004/006804 | A1 | 1/2004 |
| WO | WO2004/019817 | A1 | 3/2004 |
| WO | WO2004/021922 | A2 | 3/2004 |
| WO | WO2004/043293 | A2 | 5/2004 |
| WO | WO2005/023358 | A1 | 3/2005 |
| WO | WO2006/029370 | A2 | 3/2006 |
| WO | WO2007/035885 | A2 | 3/2007 |
| WO | WO2007/149107 | A1 | 12/2007 |
| WO | WO2008/033845 | A2 | 3/2008 |
| WO | WO2009/049677 | A1 | 4/2009 |
| WO | WO2010/026240 | A1 | 3/2010 |
| WO | WO2011/132080 | A2 | 10/2011 |
| WO | WO2012/009558 | A2 | 1/2012 |
| WO | WO2012/085916 | A2 | 6/2012 |
| WO | WO2012/094195 | A1 | 7/2012 |
| WO | WO2012/171720 | A1 | 12/2012 |
| WO | WO2013/063124 | A1 | 5/2013 |
| WO | WO2013/142386 | A1 | 9/2013 |

OTHER PUBLICATIONS

Reimers et al.; Cerebral protection with filter devices during carotid artery stenting; Circulation; 104(1); pp. 12-15; Jul. 3, 2001.

United States Patent and Trademark Office, Notice of Allowance mailed Feb. 23, 2015 in U.S. Appl. No. 14/115,088, 8 pages.

United States Patent and Trademark Office, Final Office Action mailed Dec. 17, 2014 in U.S. Appl. No. 14/115,088, 11 pages.

United States Patent and Trademark Office, Office Action mailed Jul. 29, 2014 in U.S. Appl. No. 14/115,088, 12 pages.

WIPO, International Preliminary Examining Authority (European Patent Office), International Preliminary Report on Patentability mailed Jul. 9, 2013 in International Patent Application No. PCT/EP2012/058384, 17 pages.

WIPO, European International Search Authority, International Search Report mailed Nov. 2, 2012 in International Patent Application No. PCT/EP2012/058384, 7 pages.

European Patent Office, European Search Report dated Nov. 10, 2011 in European Patent Application No. EP11165215, 7 pages.

* cited by examiner

DEVICE AND METHOD FOR DELIVERY OF MEDICAL DEVICES TO A CARDIAC VALVE

RELATED APPLICATIONS

This application is a divisional of and claims priority to U.S. patent application Ser. No. 16/560,194 filed Sep. 4, 2019, entitled Device And Method For Delivery Of Medical Devices To A Cardiac Valve, (now U.S. Pat. No. 11,992,398 issued May 28, 2024) which is a continuation of and claims priority to U.S. patent application Ser. No. 14/675,483 filed Mar. 31, 2015, entitled Device And Method For Delivery Of Medical Devices To A Cardiac Valve (now U.S. Pat. No. 10,433,946 issued Oct. 8, 2019), which is a continuation of and claims priority to U.S. patent application Ser. No. 14/115,088 filed Mar. 28, 2014, entitled Device And Method For Delivery Of Medical Devices To A Cardiac Valve (now U.S. Pat. No. 9,023,101 issued May 5, 2015), which is the U.S. National Phase of and claims priority to International Patent Application No. PCT/EP2012/058384, International Filing Date May 7, 2012, entitled Device And Method For Delivery Of Medical Devices To A Cardiac Valve, which claims benefit of European Patent Application No. 11165215.2 filed May 8, 2011 entitled Device And Method For Delivery Of Medical Devices To A Cardiac Valve; and of U.S. Provisional Application Ser. No. 61/483,689 filed May 8, 2011 entitled Device And Method For Delivery Of Medical Devices To A Cardiac Valve, all of which are hereby incorporated herein by reference in their entireties.

FIELD OF THE INVENTION

This invention pertains in general to the field of medical devices. In particular the invention relates to the positioning of catheters for the delivery of medical devices and the procedures, and more specifically to the transvascular delivery of a medical device to a cardiac valve.

BACKGROUND OF THE INVENTION

The human heart is a hollow muscular organ, responsible for pumping a large volume of blood around the human body every day. The ability to pump the blood is facilitated by several heart valves which open and close appropriately to allow blood passage through the heart. Heart valve dysfunction through natural defects or through the increasing incidence of heart disease, often requires the dysfunctional valve to be treated, with the main treatment modalities being mechanical adjustment of the valve or replacing the valve altogether. Current medical techniques are aimed at moving away from the major open heart surgery procedure, which is very traumatic for the patient, to more minimally invasive catheter based procedures, which are less traumatic, although more complicated procedures.

Catheter based procedures require precise positioning of the catheter, used to deliver for example the replacement valve, in an optimal position in relation to the cardiac valve to be treated. This is especially important as misalignment has the potential to damage adjacent cardiac structures leading to severe coronary complications. Placement of the catheter adjacent to a heart valve is hampered by the fact that the heart continues to pump throughout the procedure, giving rise to significant levels of turbulence which the catheter has to overcome to maintain its position. Furthermore, clotting of the blood leading to emboli is a continuous threat, as potentially they can lead to serious complications such as stroke.

In the US application 2009/0030510A1, it is disclosed that a significant obstacle to replacement of an aortic valve is the accurate placement of the medical device to replace the aortic valve. The solution taught to this problem is a temporary aortic valve (TAV) device. This is a catheter which has at the distal end a plurality of balloons, which can be inflated to stabilize the position of the TAV by applying pressure directly to the aortic walls of the patient. Further valve modulating tools can be passed through the lumen of the TAV. Between the balloons, blood is allowed to pass, simulating aortic valve function. This device is devised for the ablation and replacement of the aortic valve, with the balloons of the TAV fully inflated throughout the procedure to facilitate lodgment against the arterial walls.

The balloons are inflated throughout the entire medical procedure. As the balloons hamper bloodflow by restricting the available cross section for blood flow of the aortic lumen, potentially leading to leading a number of undesired issues. For instance, deliverable blood volume during the procedure may be reduced having potential dire consequences for the patient. Blood pressure may increase upstream the restriction created by the inflated balloons. The balloons may dislocate the longer time they are inflated in the aortic lumen, e.g. due to the increased blood pressure upstream thereof.

WO 2006/029370 and US 2009/0287182 discloses expandable transluminal sheaths. The distal end of the sheath is maintained in the first, low cross-sectional configuration during advancement through the atrial septum into the left atrium. The distal end of the sheath is expanded using a radial dialator, a balloon, to dialate the hole in the tissue of the atrial septum. A problem is that the device is not sufficiently stabilized for secure positioning. The radial expansion is purely for allowing the hole to heal more completely as opposed to cutting a large hole from the start.

US2005/0085842 discloses an expandable guide sheath. The sheath is advanced into a blood vessel in a contracted condition, expanded to an enlarged condition to define a lumen. The expanded lumen is for delivering fluids or instruments. Also in this prior art, a problem is that the device is not sufficiently stabilized for secure positioning. A filter is disclosed in the form of a hoop. The frame of the hoop is placed in circumferential apposition with the vessel for collecting emboli transported in the vessel.

US2003/0171803 discloses a similar hoop shaped filter basket with frame of the hoop placed in circumferential contact with the vessel wall.

US 2006/074484 A1 discloses a method and system for endovascular, endocardiac or endoluminal approach to a patient's heart. It is disclosed an embolic protection device for placement in the coronary sinuses. Guidewires terminate at the coronary sinuses and exit the patient at the thoracotomy access site, and a new valve may be inserted in the antegrade direction along the guidewires.

WO 2011/132080 A2 discloses a valvuloplasty catheter being introduced through a guide catheter until a balloon element is positioned across the aortic valve. The distal end of the guide catheter incorporates a tubular embolic filter element which is constrained in a collapsed configuration by constraint provided by an over tube. It is also discloses another type of embolic deflector mesh being applied to the upper aortic wall adjacent the aortic branches.

US 2008/147160 A1 discloses an instrument for positioning a cardiac valve prosthesis in a vessel including a wire element to slidingly guide the valve prosthesis towards an implantation site and an expandable element coupled to the wire element. The expandable element is expandable in the vessel to position the wire element in association with the implantation site.

WO 2005/023358 A1 discloses an apparatus and method to provide distal protection while accessing blood vessels within a patient's vasculature. A flexible sheath and distal protection element, e.g., a balloon or filter, are carried by a catheter. The sheath may be located on a distal region or may extend along the entire length of the catheter.

US 2010/211095 A1 discloses an embolic deflector that deploys via brachial or radial approach into the aorta to cover the ostia of the brachiocephalic and left common carotid artery.

Hence, improved or alternative medical devices and procedures for stabilizing the introducer sheath during cardiac valve replacement would be advantageous, in particular allowing for increased cost-effectiveness, and/or patient safety.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical device and a method according to the appended patent claims.

The present invention is an introducer sheath with an embolic protection unit that protects the side branch vessels of the aortic arch to decrease the risk for embolism, from for example debris emanating from the treatment of a stenotic valve, while allowing positioning of the sheath at the cardiac valve and delivering of medical devices therethrough. In addition, the introducer sheath overcomes the positional problems that current catheters face, by using a locking system which locks the catheter to maintain it at the desired anatomical position. In addition to maintaining the position, the invention is so devised so that interference with the blood flow is minimal.

According to a first aspect, a catheter device is provided for transvascular delivery of a medical device to a cardiac valve region of a patient. The catheter device comprises an elongate sheath with a lumen and a distal end for positioning at a heart valve, and a second channel that extends parallel to, or in, said elongate sheath, an expandable embolic protection unit, such as a filter, wherein at least a portion of the expandable embolic protection unit is arranged to extend from an orifice of the second channel, wherein the embolic protection unit is non-tubular, extending substantially planar in the expanded state for covering ostia of the side branch vessels in the aortic arch.

In a second aspect, a method of transvascularly delivering a medical device to a cardiac valve of a patient is provided. The comprises providing and minimally invasively introducing a catheter comprising an elongate sheath with a lumen in a relaxed state into said vascular system; navigating a distal end of said elongate sheath through said vascular system to said cardiac valve; expanding an embolic protection unit from a second channel in said sheath to cover ostia of the side branch vessels in the aortic arch and to stabilize a distal end of said sheath at the cardiac valve, delivering a medical device through the lumen of said locked elongate sheath to said heart valve while said embolic protection unit covers said ostia.

Further embodiments of the invention are defined in the dependent claims, wherein features for the second and subsequent aspects of the invention are as for the first aspect mutatis mutandis.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
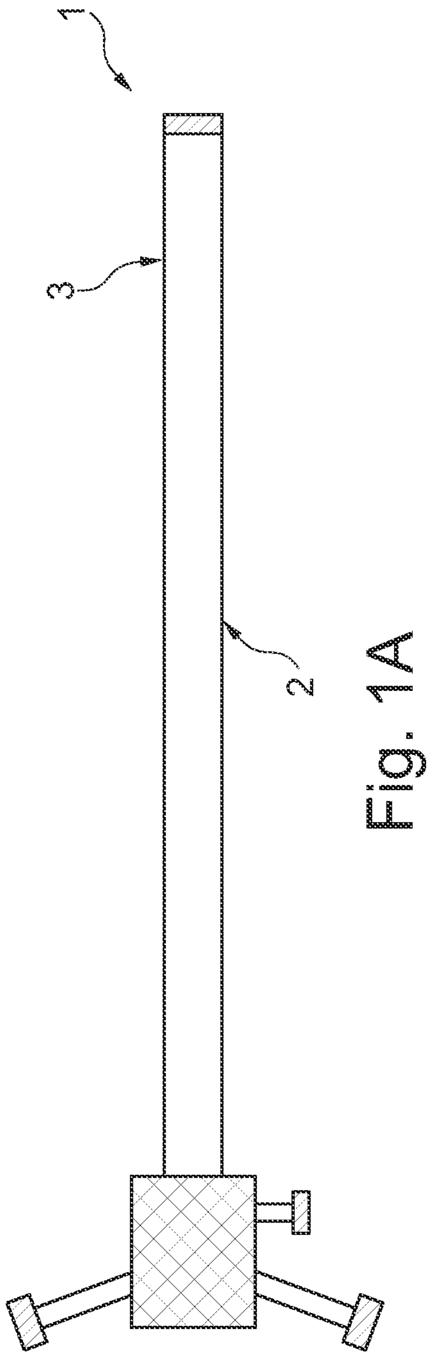
FIG. 1A is a schematic illustration of an elongate sheath connected to a hemostatic valve.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1B:
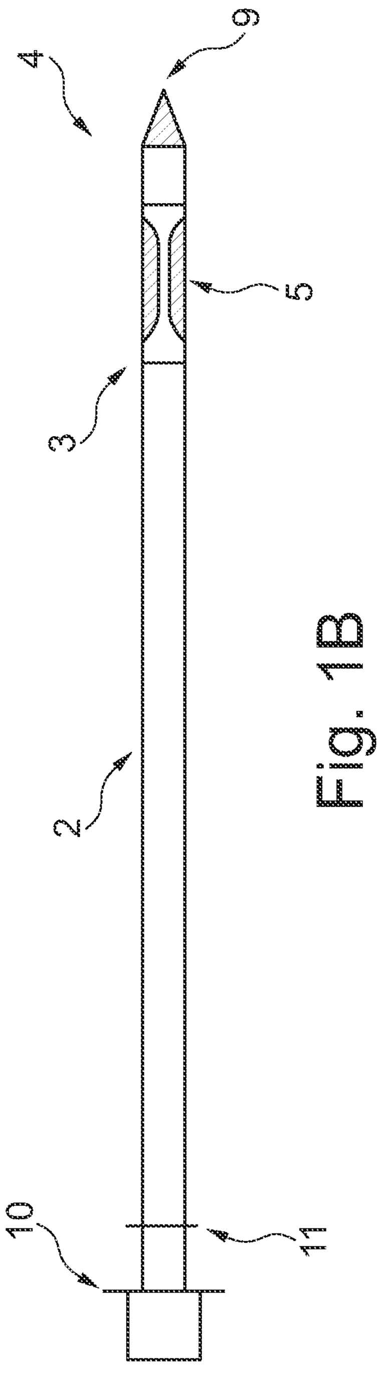
FIG. 1B is a schematic illustration of an elongate member, with the radially expandable units in the collapsed configuration.

In an embodiment of the invention according to FIG. 1A, a catheter device 1 for transvascular delivery of a medical device to a cardiac valve region 6 (see e.g. FIG. 4D) of a patient is shown. The catheter device comprises an elongate sheath 2 with a lumen and a distal end 3. In addition in FIG. 1B an elongate member 4 is provided with a distal end portion 9 comprising a plurality of radially expandable units 5. The end portion 9 may include an obturator. The expandable units 5 are arranged for temporarily positioning the elongate sheath 2 in relation to the cardiac valve 6, FIGS. 4B and 4F. The elongate member 4 is retractably insertable into the lumen of the elongate sheath 2 and the elongate sheath 2 comprises releasable locking members for controllably locking the elongate sheath 2 in a shape at least partly along its length from a relaxed state (See FIG. 3B, and FIG. 4A-B, 4F) to a locked state (See FIG. 3C-D, and FIG. 4D-E, 4G-H) when positioned in relation to the cardiac valve 6 by the expandable units 5.

The elongate sheath 2 depicted in FIG. 1A is designed to be deliverable transvascularly in the relaxed state which facilitates optimal flexibility when transiting through the vasculature. When at the desired anatomical location the elongate sheath 2 is able to transit from the relaxed state to the locked state by activation of the locking members, when positioned in relation to the cardiac valve 6, as seen in FIG. 4D-E, by said expandable units 5, which facilitates optimal stabilization of the catheter 1 for subsequently affixing the medical device to the heart valve 6.

Figure 4A:
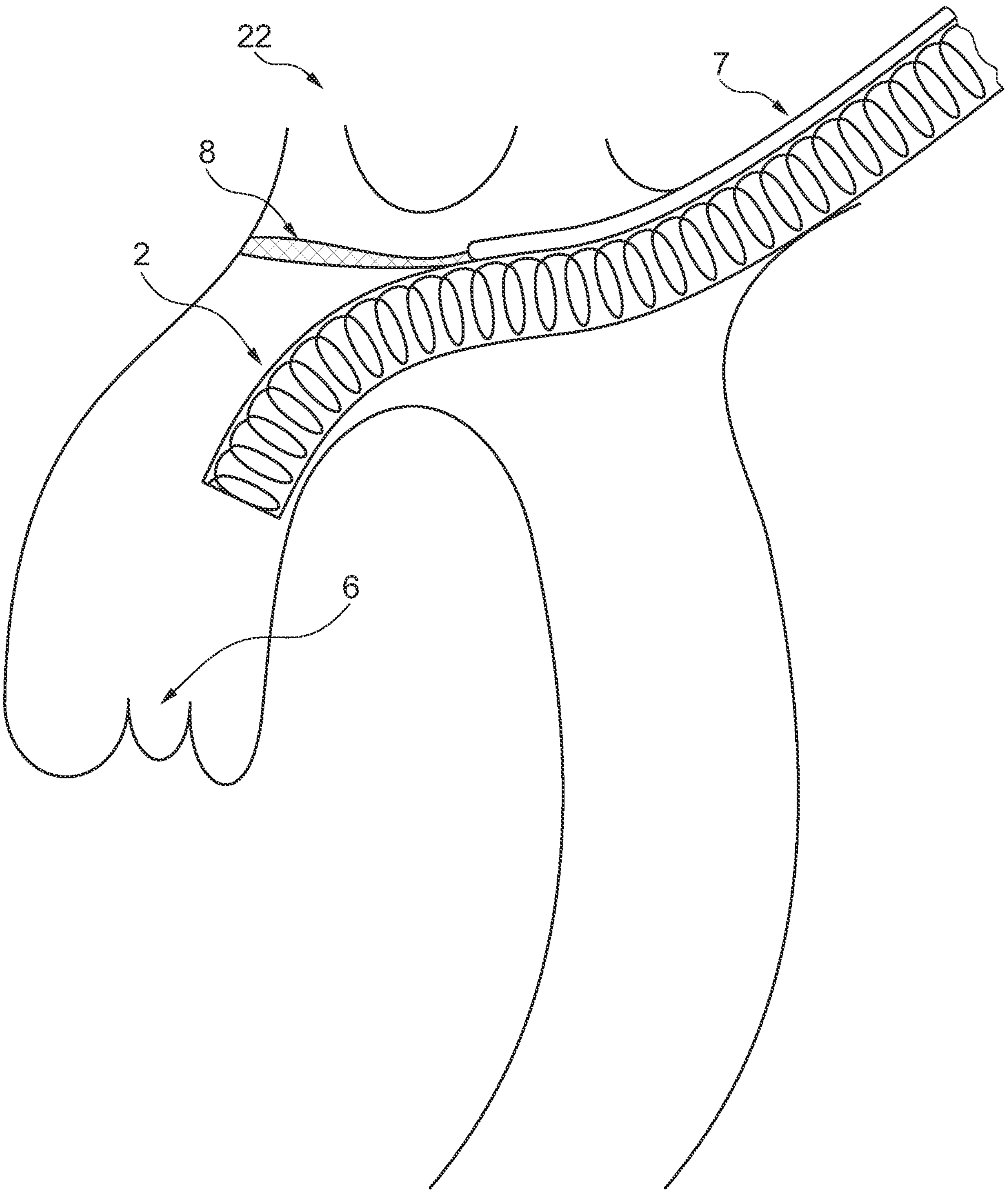
FIG. 4A is a schematic illustration of the elongate sheath delivered transaxillary to a cardiac valve, where an embolic protection filter is deployed, and the sheath is in a relaxed state.
Figures 4B, 4C:
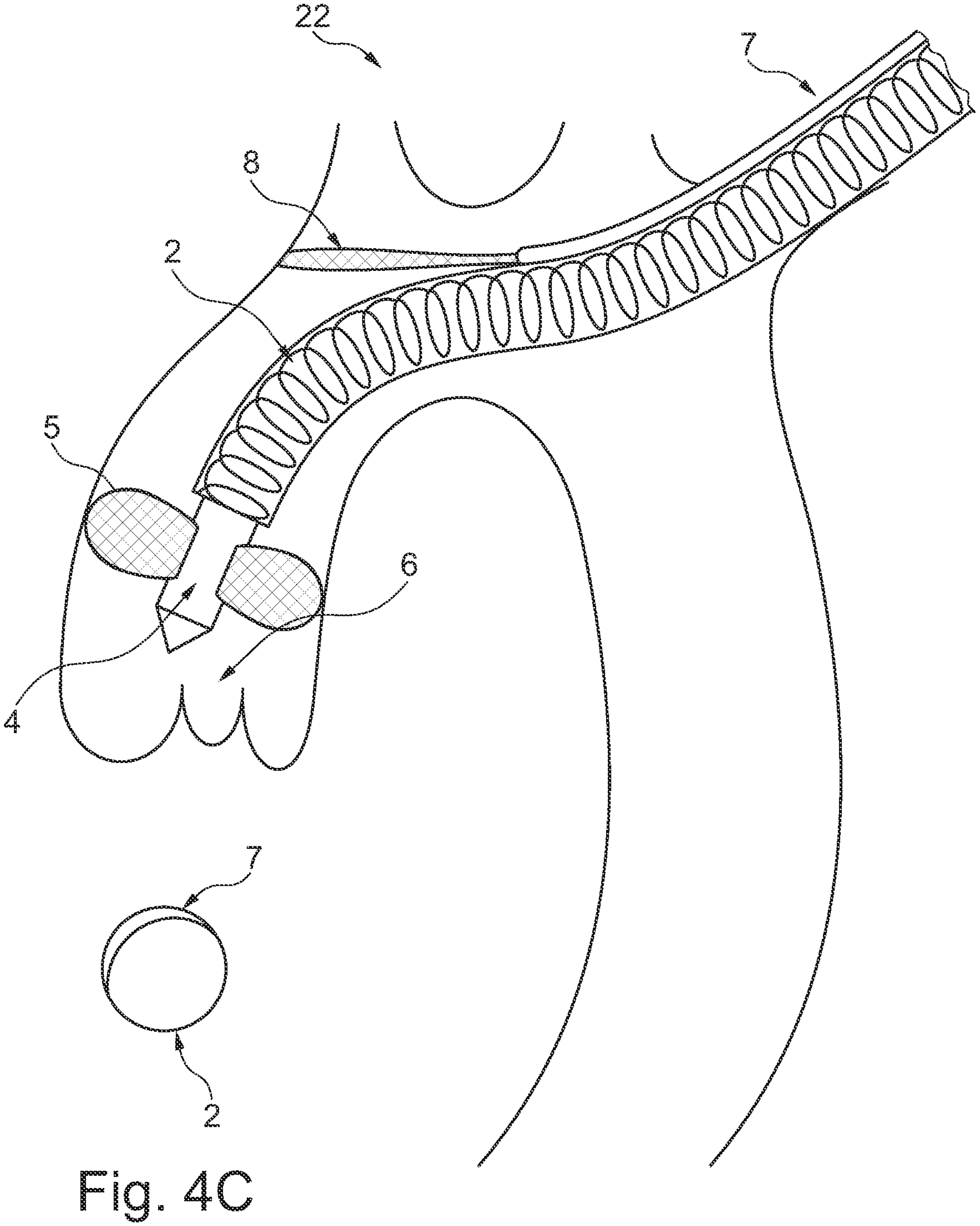
FIG. 4B is a schematic illustration where the relaxed sheath is positioned in relation to the cardiac valve by expandable units of an elongate member extending outside the distal end of the sheath.
FIG. 4C is a schematic illustration of the cross sectional view of the elongate sheath incorporating a second channel for delivering the embolic protection filter.
Figure 4D:
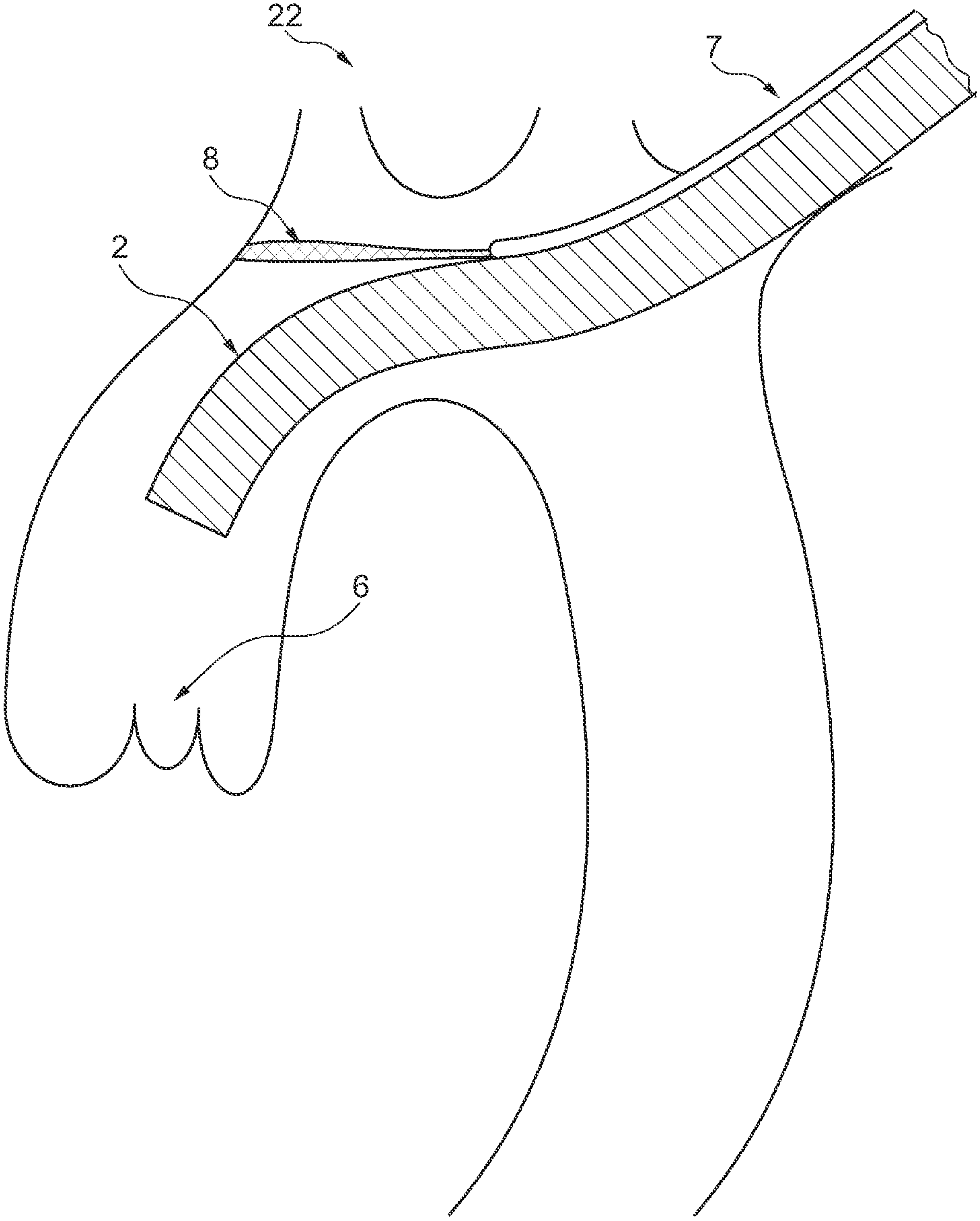
FIG. 4D is a schematic illustration of the elongate sheath delivered transaxillary to a cardiac valve, and the sheath is in the locked configuration arranged relative to an aortic cardiac valve, and the expandable units being withdrawn after positioning the sheath.
Figure 4E:
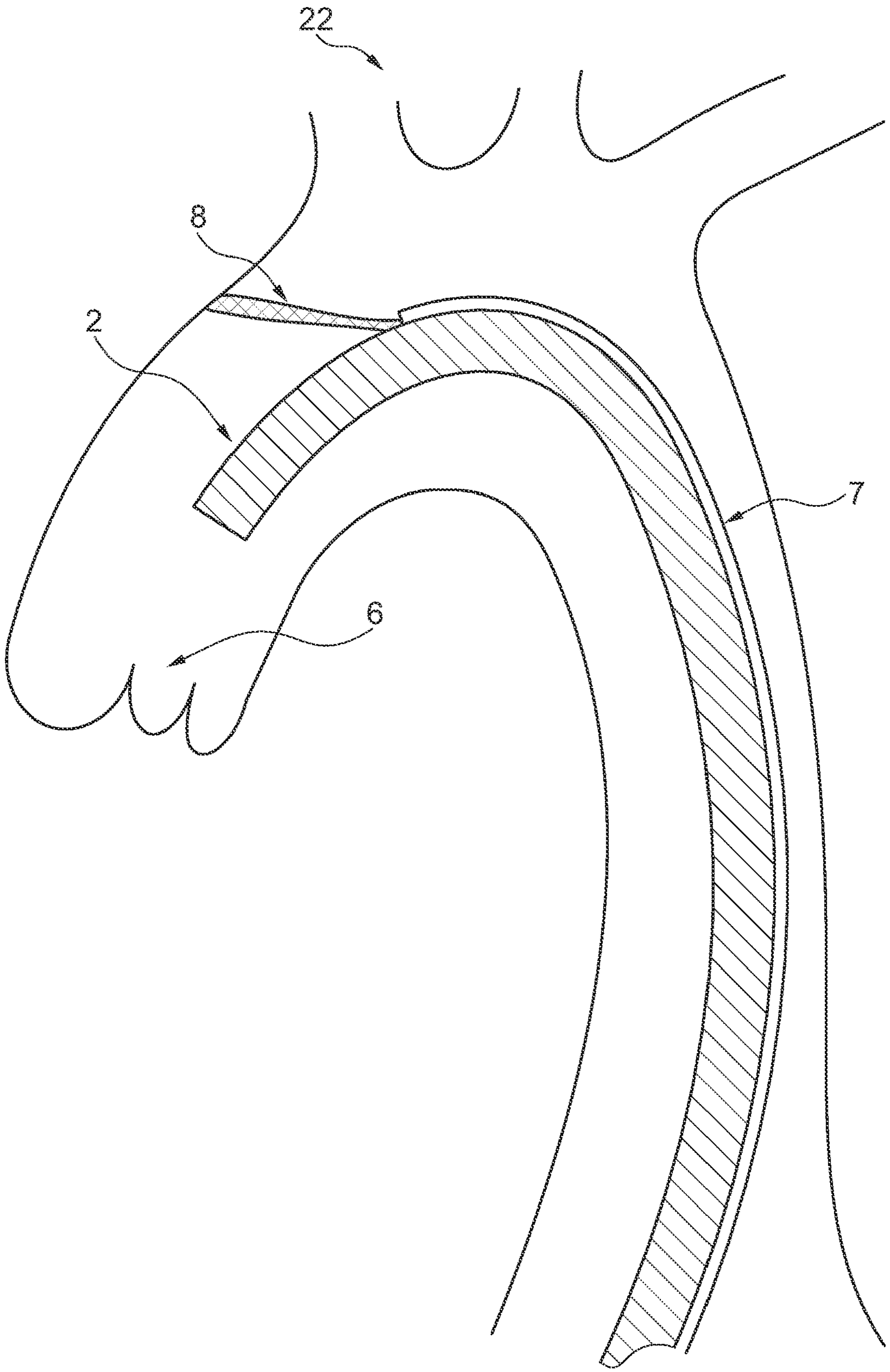
FIG. 4E is a schematic illustration of the elongate sheath delivered transfemorally to a cardiac valve, where an embolic protection filter is deployed and the sheath in the locked configuration.

FIG. 4A shows the elongate sheath inserted in its relaxed shape. FIG. 4B shows the radially expandable units 5 in their expanded configuration, i.e. outside the elongate sheath 2, which positions the elongate sheath 2 centrally over the valve 6. The expandable units 5 expand out of the elongate member 4, which extends beyond the distal end of the sheath 2. Thereafter the elongate sheath 2 is brought to its locked state by locking members, and the elongate member 4 is retractable from the lumen of the elongate sheath 2 together with the plurality of radially expandable units 5 when collapsed, as seen in FIGS. 4D-E. The sheath 2 is now positioned and stabilized over the valve 6. This overcomes the problems in prior art with insufficient stabilization and lack of accurate positioning. Merely providing an expandable catheter could not provide stabilization as with the locking members of the sheath 2. Expandable catheters have another purpose, which is providing an accessible lumen or dilating septum punctures. Further, expandable members of previous catheters are merely for providing aforementioned expansion and not for positioning the catheter centrally over a valve as provided by catheter 1. When the elongate sheath 2 is locked and, when the elongate member 4 is retracted, the lumen of the elongate sheath 2 is accessible for delivery of a medical device to the cardiac valve 6 region.

Figure 4F:
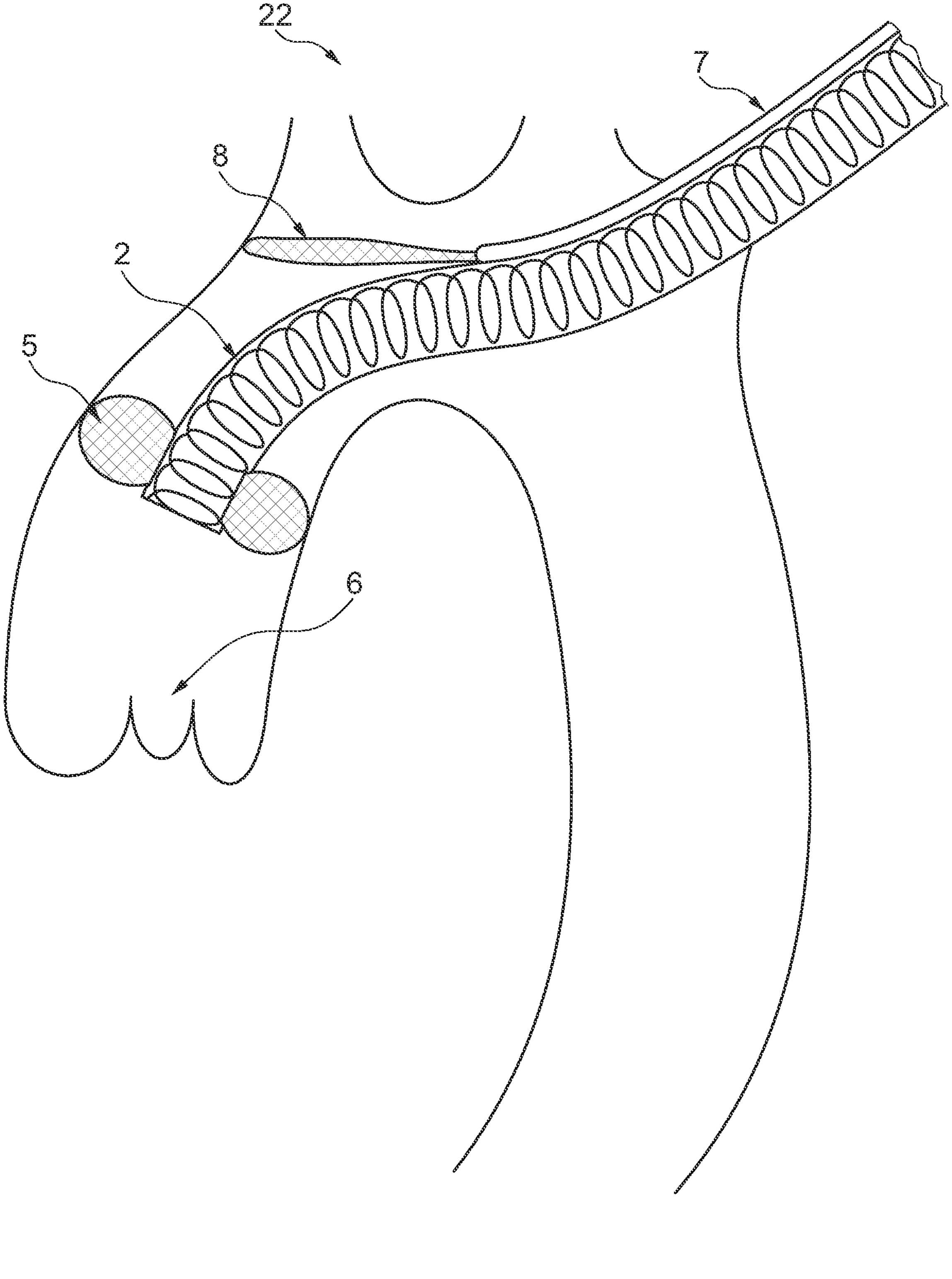
FIG. 4F is a schematic illustration of the elongate sheath delivered transaxillary to a cardiac valve, and where the relaxed sheath is positioned in relation to the cardiac valve by expandable units of the sheath.

Alternatively, or in addition, expandable units, such as balloons may be arranged on the outside of the sheath 2. The expandable unit may be integrally formed with the sheath, as seen in FIG. 4F. Thus, the expandable units do not affect the cross section of the lumen of sheath 2. Upon returning to the unexpanded state, e.g. by deflating balloons of the expandable units 5, a delivery of a medical device through the catheter lumen may be made without the need to retract the expandable units 5.

The expandable units provide for a defined positioning of the distal end of the catheter sheath 2 in an anatomical structure, like a blood vessel, an atrium or cardiac chamber, relative a cardiac valve. This allows for a precision delivery of a medical device through the catheter device. Movements of certain anatomical structures are very limited over the cardiac cycle. For instance the aortic arch is relatively stable and the locked catheter will stay substantially in the same spatial orientation, direction, and distance to the cardiac valve as during the final positioning provided by the expanded expandable units 5.

The catheter may thus be positioned relative a cardiac valve in an anatomical structure.

The catheter may be locked in the locked configuration along its entire length. Alternatively, it may only be locked along a distal portion thereof. A distal portion may for instance be the portion arranged in the ascending aorta, the aortic arch and the descending aorta, as shown in FIG. 4E. The catheter may comprise an embolic protection unit 8, such as a embolic protection filter 8. The embolic protection unit 8, when protruding out of the second lumen 7 and being in apposition against the surrounding vessel wall, may further contribute to stabilizing the distal end of the locked catheter in place relative to the cardiac valve. Hence, when the embolic protection unit 8 is expanded it will function as an anchor to the sheath because it prevents movement of the sheath 2 in the aortic arch due to the second channel 7, from which the embolic protection unit expands, is fixed to the sheath. The delivery unit 13 for the embolic protection unit 8 has sufficient rigidity to allow an anchoring function for the sheath 2. The embolic protection unit 8 provides stabilization and anchoring of the sheath 2 irrespectively whether the sheath 2 is in a relaxed state or in a locked state. Further, The embolic protection unit 8 provides stabilization and anchoring of the sheath 2 irrespectively whether expandable units 5 are used. Hence, it is not essential for the sheath 2 to have the locking members, the elongate member 4, or the expandable units 5, in order to provide the advantageous effects as described, see further below.

FIG. 4D is a schematic illustration of the elongate sheath delivered transaxillary to a cardiac valve, here the aortic valve 6. The embolic protection filter 8 is deployed, and the sheath 2 is in the locked configuration arranged relative to an aortic cardiac valve 6.

FIG. 4E is a schematic illustration of the elongate sheath delivered transfemorally to a cardiac valve, where an embolic protection filter is deployed and the sheath in the locked configuration.

In FIGS. 4D and 4E, the expandable units 5 are not shown, as they are either retracted from the sheath, or returned to their low profile unexpanded/collapsed configuration in the sheath.

Figure 4G:
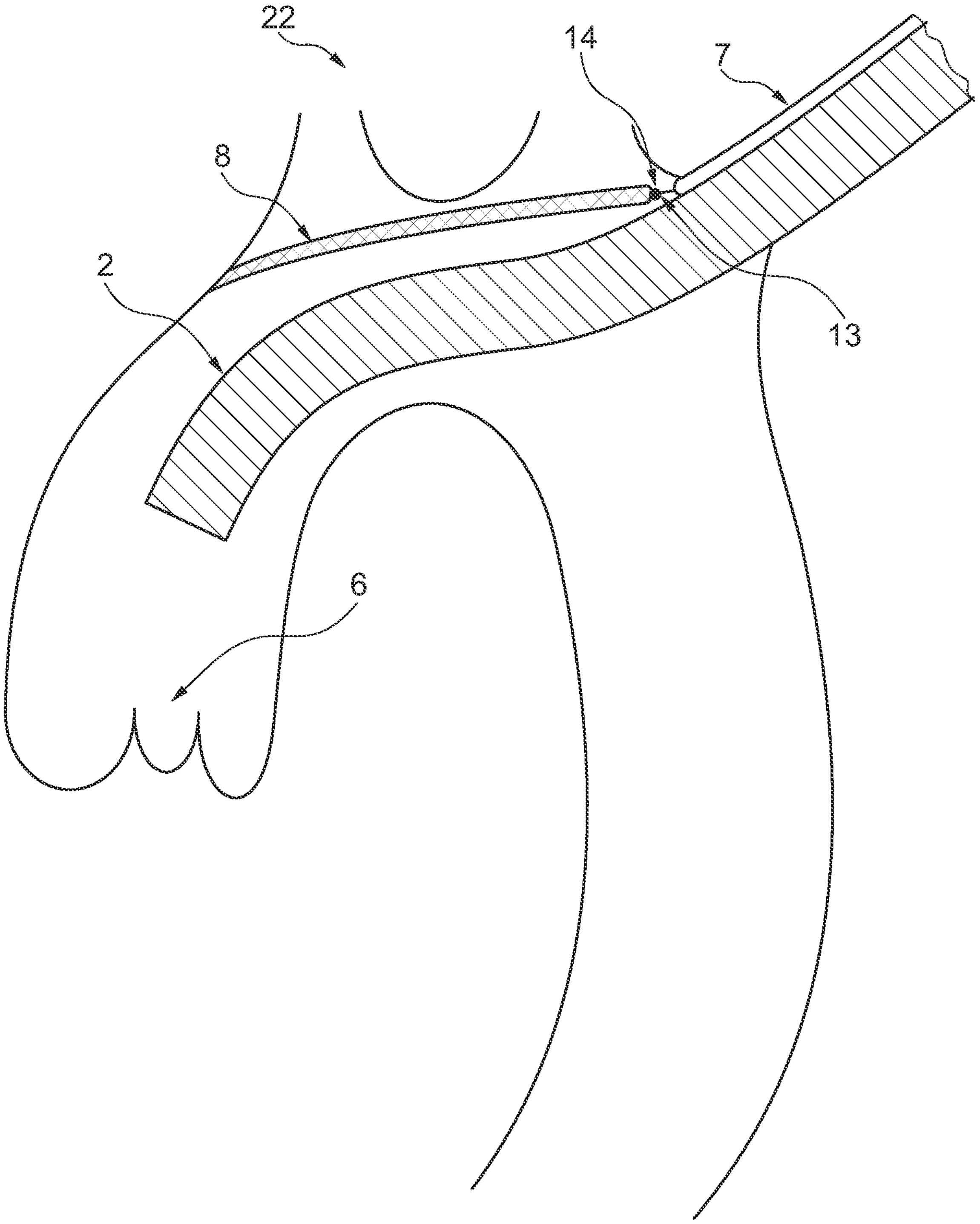
FIG. 4G is a schematic illustration of the elongate sheath delivered transaxillary to a cardiac valve, and where an embolic protection filter is deployed over the vessels in the aortic arch via a second channel of the sheath.
Figure 4H:
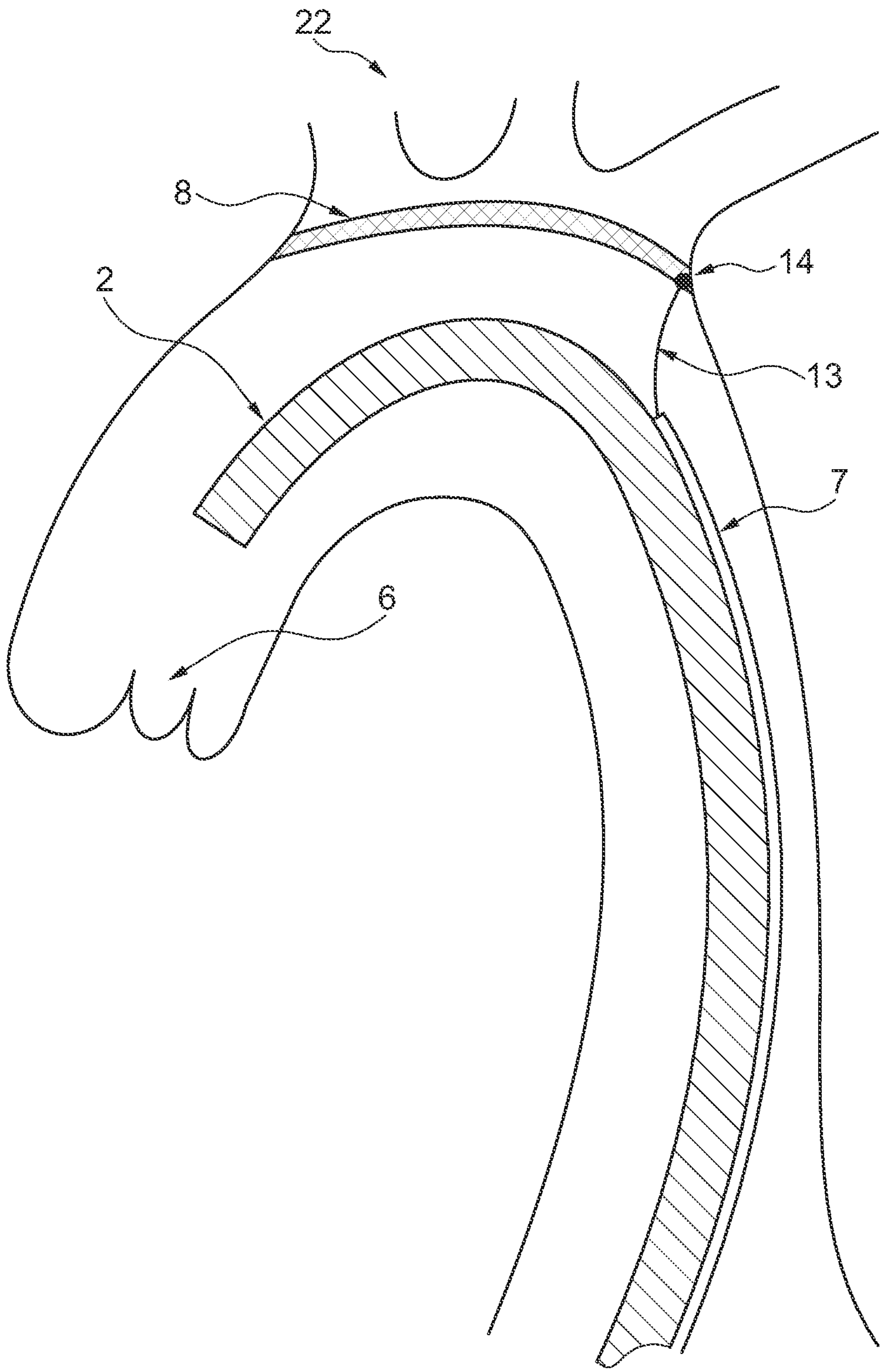
FIG. 4H is a schematic illustration of the elongate sheath delivered transfemorally to a cardiac valve, and where an embolic protection filter is deployed over the vessels in the aortic arch via a second channel of the sheath.

In FIG. 4G-H the embolic protection filter 8 is positioned over two or three of the vessels in the aortic arch, respectively.

In all configurations shown in FIGS. 4A-B, 4D-H, the side vessels 22 are effectively protected from embolic particles entering from the aortic arch. Embolic particles are carried with the blood flow past the embolic protection device along the aortic arch to anatomical structures that are less sensitive than e.g. the brain to which some of the side vessels 22 lead the blood flow. Embolic protection units may be filter units in which the embolic particles are caught. Alternatively, or in addition, the embolic protection units may provide for the particles to slide along the protection unit, but not pass it or fasten in it.

In embodiments, such as illustrated in FIG. 4A-H a catheter 1 having a second channel 7 that extends parallel on the outer portion or the inner portion of the elongate sheath 2 is depicted. This channel 7 allows for the delivery of further units for example an embolic protection device 8 or liquids to aid the procedure to place the medical device, when the lumen of the elongate sheath 2 is used for the elongate member 4 or medical device.

The second channel 7 may be an integral part on the inside or outside of the elongate sheath 2. This has the advantage of being relatively cheap to manufacture by an extrusion method.

In FIGS. 4A-H, an expandable embolic filter 8 embodiment is depicted. The embolic protection or filter device 8 may be extended before extending the aforementioned expandable units 5. This potentially enhances patient safety by capturing any emboli such as plaque debris produced from the treatment of a stenotic valve, and thus reduces the chance for serious complications such as stroke. In these figures at least a portion of the expandable embolic filter 8 extends from the orifice of the side channel 7 through which the embolic filter 8 is passed. The embolic filter may be of the type as disclosed in WO 2010/026240, which is incorporated herein in its entirety for all purposes. The embolic filter unit may be non-tubular, extending substantially planar in the expanded state. This provides for a compact device and efficient blocking of side branch vessels in the aortic arch from embolies. Interaction with the side walls in the aortic arch is therefore also kept at the minimum, avoiding scraping off further debris to be transported with the blood stream. Simultaneously, the aortic arch is kept open for unrestricted navigation of the sheath 2. Hoop shaped baskets in previous devices scrapes against the vessel wall and blocks a substantial portion of the navigational space in the aortic arch.

Extending "planar" in this context means that the thickness of the device is substantially smaller than the longitudinal extension thereof. Moreover, "planar" means such dimensions perpendicular to the longitudinal extension of the protective material, that blood flow through the aortic arch is not hindered by the protective device.

By having a second channel in the sheath 2, the distal end of the sheath can be positioned appropriately at the valve, by the stabilizing and anchoring effect of the protection unit 8 extending from the second channel, while medical device can be delivered through the lumen of the sheath without any hindrance from the protection unit 8 or e.g. expandable units such as balloons, while at the same time the side branch vessels of the aortic arch are protected from embolies that may be transported in the blood stream from the procedure performed at the valve.

The catheter device 1 may comprise a delivery unit 13 connectable to the embolic filter unit 8 at a connection point 14, as illustrated in FIGS. 4G-H. The connection point 14 is arranged off-centre at the embolic filter unit such that the delivery unit 13 is connectable off-center to the embolic filter unit 8. The off centre position of the embolic filter unit is advantageous for deploying it with the sheath 2 via the delivery unit 13, while efficiently protecting the carotid arteries from embolies, when carrying out the intervention. Blood flow is kept open efficiently by such compact device. The term "off centre" used in the context of the present application means eccentric, or not arranged or located in a center. The center is e.g. a center of a circular unit, a focal point of an elliptical unit, a point on a center line, such as a longitudinal center line of an elongated unit, etc. A periphery of a unit is located "off centre" as it is arranged at a distance in relation to a center of the unit.

Figure 2A:
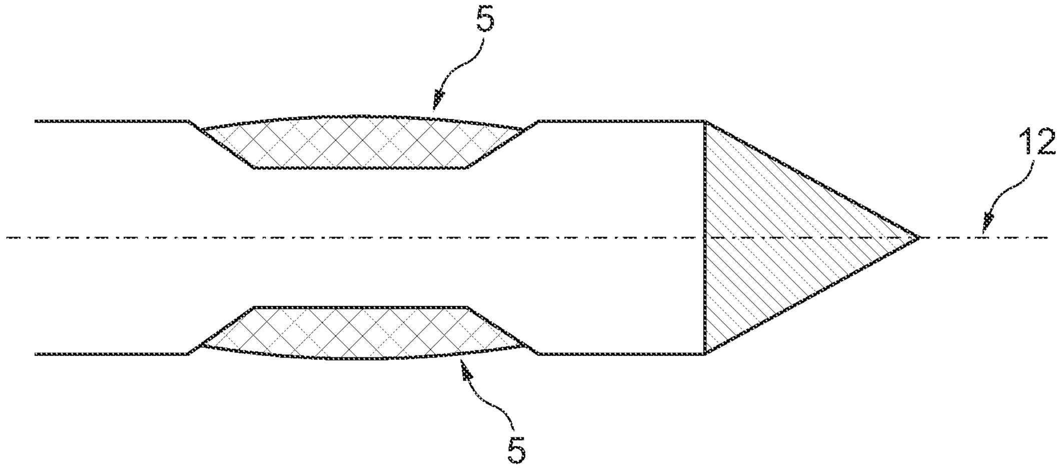
FIG. 2A is a schematic illustration of the distal end portion of the elongate member with the radially expandable units in the collapsed configuration.
Figure 2B:
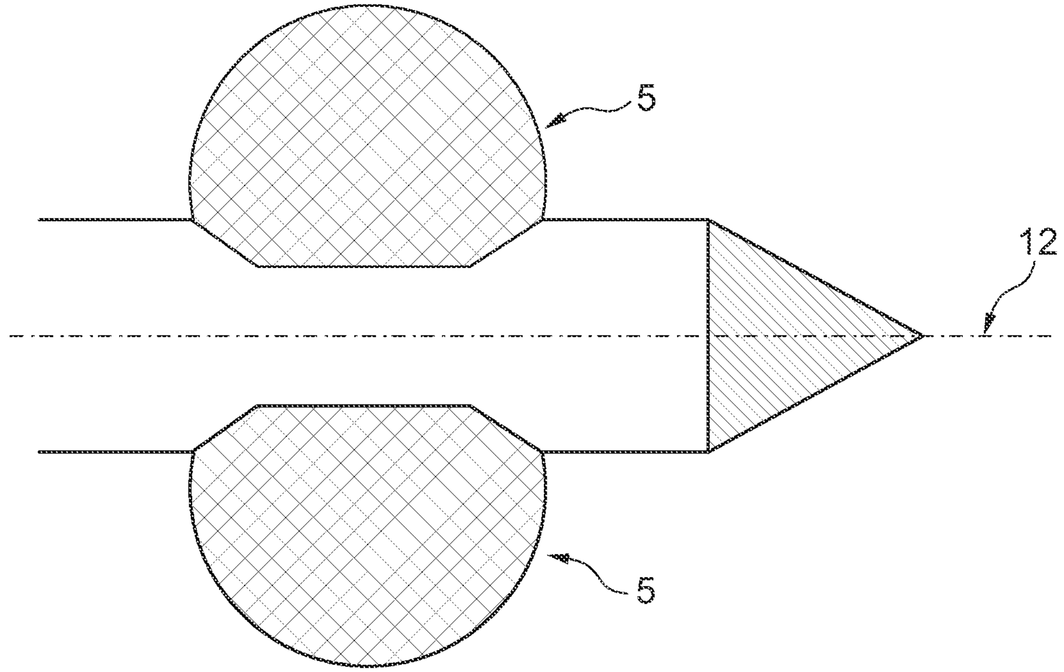
FIG. 2B is a schematic illustration of the distal end portion of the elongate member with the radially expandable units in the expanded configuration.
Figure 2C:
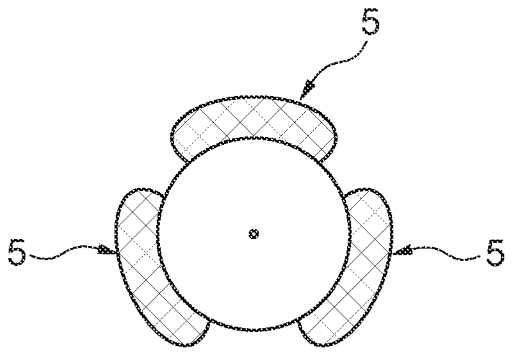
FIG. 2C is a schematic illustration frontal view of the distal end portion of the elongate member with the radially expandable units in the collapsed configuration.
Figure 2D:
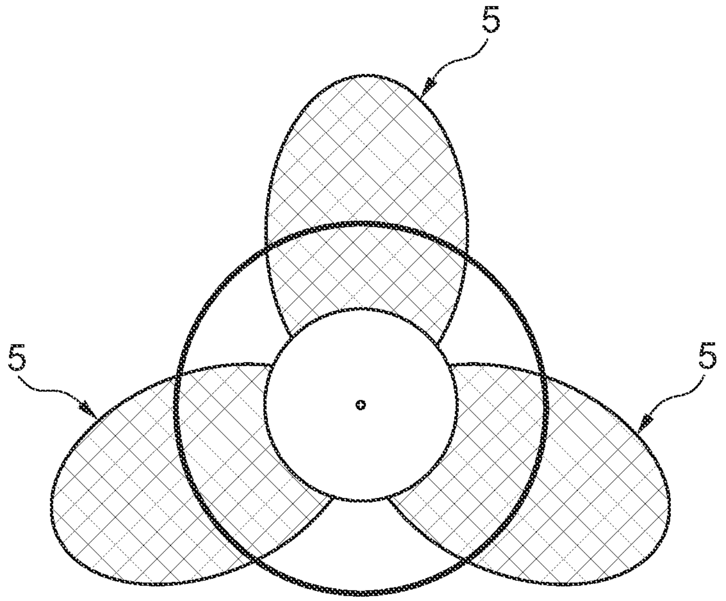
FIG. 2D is a schematic illustration frontal view of the distal end portion of the elongate member with the radially expandable units in the expanded configuration.
Figure 3A:
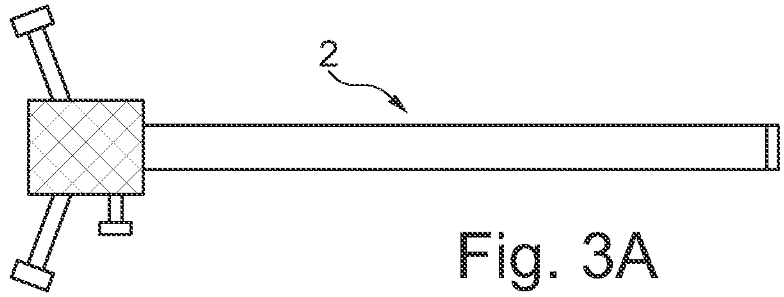
FIG. 3A, 3B, 3C, 3D are schematic illustrations of embodiments of the elongate sheath in the flexible, unlocked configuration.
Figure 3B:
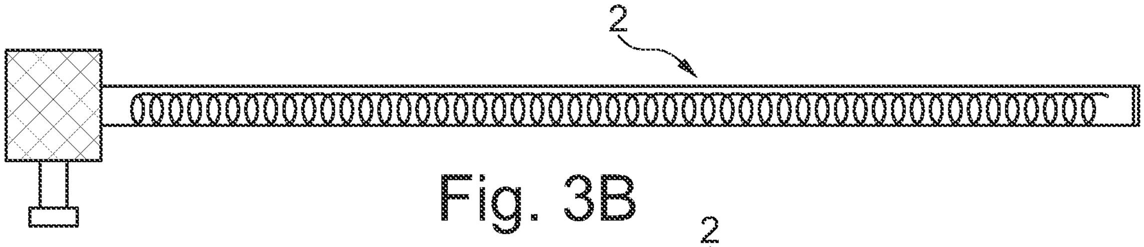
Figure 3C:
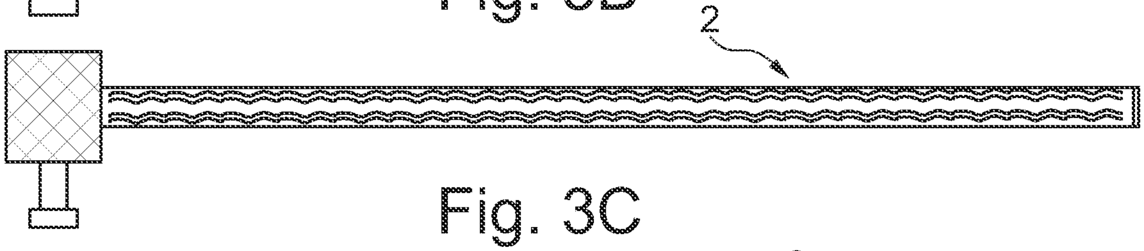
Figure 3D:
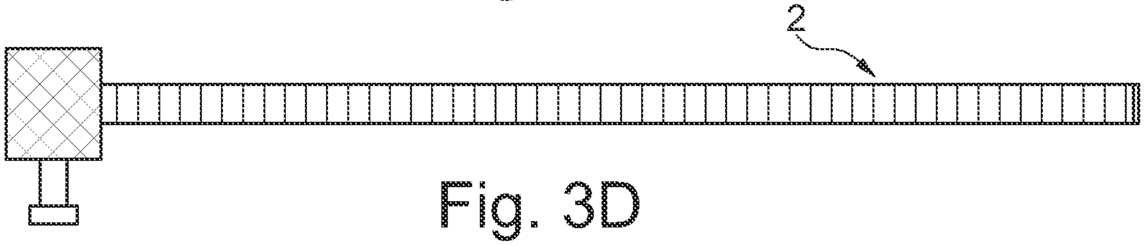
Figure 3E:
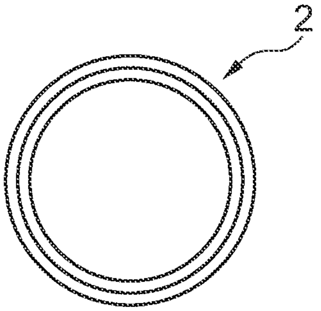
FIG. 3E is a schematic illustration of the cross sectional view of the elongate sheath in the unlocked state.
Figure 3F:
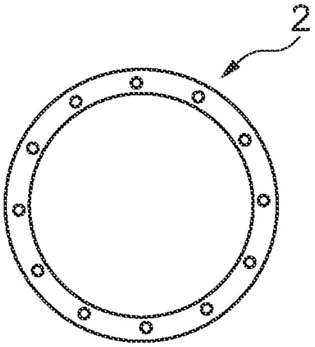
FIG. 3F is a schematic illustration of one embodiment of the cross sectional view of the elongate sheath in a locked state.
Figure 3G:
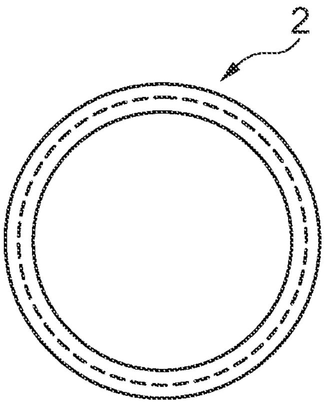
FIG. 3G is a schematic illustration of another embodiment of the cross sectional view of the elongate sheath in the locked state.

The elongate member 4 may be comprised of three balloons positioned radially equidistant around the longitudinal axis (See FIGS. 2C and D). Fewer or more balloons are possible, as well as alternative expansion units such as expandable mechanical levers, or swellable units for example retractable sponges. The expansion units 5 allow for optimal positioning of the elongate sheath 2 in relation to the aforementioned cardiac valve 6. The multiple balloon expansion unit can be expanded (See FIG. 2D) using a variety of means for example using a fluid means or where appropriate gaseous means. The balloons can also be individually or simultaneously expanded as well as inflated to differing pressures independently of the other expanding units.

Alternatively, the elongate member 4 is retractably inserted into the elongate sheaths 2 lumen to a length equal to the distance between the distal end 9 and the second proximal marker 10. In this embodiment proximal markers 10 and 11 are used to guide the positional orientation of the distal end portion 9 and thus provide for optimal alignment of the expandable units 5 with the portion of the elongate sheath 2 to be expanded. This facilitates safe positioning at the desired valve region.

In a further embodiment the elongate sheath 2 is comprised of radiopaque material, facilitating visualization of the elongate sheath 2 which provides for optimal positioning of the elongate sheath 2 for delivery of the medical device. Alternatively radiopaque fiducial markers on the elongate sheath 2 can be used for optimal positioning of the sheath 2 within the body of the patient.

The embodiment shown in FIGS. 2A and B, includes a guide wire 12 which is firstly positioned within the patient which facilitates optimal transit of the elongate sheath 2 and elongate member 4 to the desired anatomical site.

In the embodiments of FIGS. 3-4, the locking units may comprise releaseable latches although any one from draw strings, squeezing mechanisms, or the like could be envisaged as being used to lock the elongate sheath 2 in a locked state, i.e. a rigid or semi-rigid state of the sheath that allows the sheath 2 to maintain a specific curvature, i.e. reduction in flexibility, and thereby secure its position relative to the anatomy, as seen in e.g. FIG. 4D-E. Further, thermal, electrical, magnetic or chemical properties of the material of the locking units or the elongate sheath 2 itself may provide variable flexibility for changing between a locked state and a relaxed state.

In a specific embodiment, the elongate may be expanded when in locked configuration. Releasing of locking units when the elongate sheath 2 is in an expanded state locks the elongate sheath 2 in the expanded state and thus retains the optimal position for medical device positioning through the procedure.

The locked elongate sheath 2 may be used in medical procedures to deliver a medical device to the cardiac valve 6, which could include an artificial heart valve prosthesis, an annuloplasty device or leaflet clips.

Figure 5:
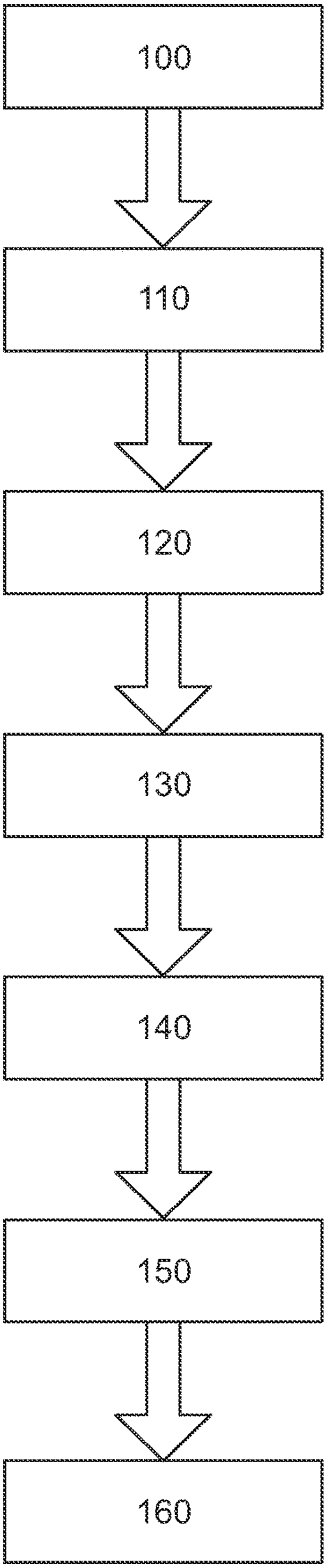
FIG. 5 is a flowchart for a method of implanting a medical device.

The elongate sheath 2 maybe a constituent of a medical system devised for transvascularly delivering a medical device to a cardiac valve 6 of a patient. The method as depicted in FIG. 5 initially comprises 100 minimally invasively either transfemorally (See FIG. 4E) or transaxillary (See FIG. 4D) introducing a catheter 1 comprising an elongate sheath 2 with a lumen in a relaxed state into the patients vascular system. Step 110 involves the distal end 3 of said elongate sheath 2 being navigated through the vascular system to the desired cardiac valve, FIG. 4A. The next step in the system 120, involves the elongate member 4 with a distal end portion 9 comprising a plurality of radially expandable units 5, being inserted into the lumen of the elongate sheath 2, whereupon it is advanced through the elongate sheath 2 to the distal end of the elongate sheath 2, FIG. 4B. Alternatively, expandable units 5 of the sheath may be expanded at this stage (without introducing an elongate member 4 into the sheath, FIG. 4F. Whereupon step 130 is initiated which involves the plurality of radially expandable units 5, being radially expanded to temporarily position in relation to the cardiac valve 6 the elongate sheath 2, (See FIGS. 4B and F).

Following positioning, the locking members of the catheter are released to maintain the elongate sheath 2 in a locked state (step 140). Step 150 of the system can then be performed whereby the expandable units 5 are then retracted and the elongate member 4 is withdrawn from the lumen of the elongate sheath 2, FIG. 4D-E. Alternatively, the expandable units 5 of a sheath 2 are brought back to the non-expanded state.

The embolic protection unit as shown in FIGS. 4A-H, may then be advanced out of the second channel 7. In this manner, side vessels are protected from embolic material, such as debris.

A medical device can now be delivered through the lumen of the locked elongate sheath 2 to the heart valve 6. This delivery is done with high spatial precision. Blood flow in the lumen around the locked sheath 2 is affected less than with expanded expandible units 5.

The medical device may for instance be a cardiac valve repair or replacement device.

When the medical device is delivered, release of the locking members to return the elongate sheath 2 to the relaxed state can now be performed (step 160) with the subsequent withdrawal of the elongate sheath 2 in the relaxed state from the vasculature of the patient.

The embolic protection unit as shown in FIGS. 4A-H, may be retracted prior or after the release of the locking members.

Locking of the elongate sheath 2 in the locked state (FIG. 3B-D) comprises releasing the locking members for controllably locking the elongate sheath 2 when positioned in relation to the cardiac valve 6 by the expandable units 5. This serves to retain the optimal position for delivery of the medical device during the procedure.

To ensure the optimal positioning of the elongate member 4 when it is inserted into the elongate sheath 2, the elongate member 4 is inserted to a length which is equal to the distance between the distal end and the second proximal marker 10 of the elongate member 4. Primarily the elongate sheath 2 will be centrally positioned in relation to the cardiac valve 6, which facilitates optimal delivery of the medical device, although other positions off-center could also be desirable.

The medical system is primarily used for the delivery of a medical device to be affixed to the particular cardiac valve 6, which include the aortic and mitral valves of a patient. After delivery of the medical device to the cardiac valve 6, the medical device delivery system is withdrawn through the lumen of the locked elongate sheath 2, which may be aided if the elongate sheath 2 is in an expanded state. After removal of the medical device delivery system, the elongate sheath 2 in said locked state transits to said relaxed state which facilitates enhanced retraction of the elongate sheath 2.

The present invention has been described above with reference to specific embodiments. However, other embodiments than the above described are equally possible within the scope of the invention. Different method steps than those described above, may be provided within the scope of the invention. The different features and steps of the invention may be combined in other combinations than those described. The catheter may be positioned and locked in other cardiac anatomical structures than illustrated. Medical devices delivered through the catheter sheath may be any medical device to be delivered to the cardiac valve tissue. The scope of the invention is only limited by the appended patent claims.

The invention claimed is:

1. A method for transvascularly delivering a medical device to a site of a cardiac valve of a patient, said method comprising:
- providing
  - a first lumen having a proximal end and a distal end, said distal end of said first lumen being configured for positioning at a heart valve,
  - a second lumen arranged to extend parallel to the first lumen along a portion of said first lumen between said proximal end and said distal end of said first lumen, and having an orifice at a distal end of said second lumen, and
  - an expandable embolic protection filter having an unexpanded delivery shape and an expanded shape, wherein said embolic protection filter is configured to be expanded from said orifice of said second lumen;
- introducing said second lumen into a vascular system;
- navigating said distal end of said second lumen through said vascular system to the site of said cardiac valve;
- expanding, from said orifice at said distal end of said second lumen, at least a portion of said expandable embolic protection filter, thereby covering an ostia of side branch vessels in an aortic arch;
- introducing said first lumen into said vascular system;
- navigating said distal end of said first lumen through said vacular system to said site of said cardiac valve;
- delivering the medical device through said first lumen to said site of said heart valve while said embolic protection filter covering said ostia.

2. The method of claim 1, wherein said expanding of said embolic protection filter comprises expanding said embolic protection filter to a non-tubular shape over said ostia.

3. The method of claim 1, wherein the embolic protection filter is configured to cover all the ostia of said side branch vessels in the aortic arch when extended from said orifice of the second lumen.

4. The method of claim 1, further comprising delivering said embolic protection filter through said second lumen using a delivery unit connected to said embolic protection filter.

5. The method of claim 4, wherein said embolic protection filter is connected off-center to said delivery unit.

6. The method of claim 1, wherein said embolic protection filter is configured to capture or deflect embolic material.

7. The method of claim 1, wherein said embolic protection filter is configured to allow blood to flow from the aortic arch into said side branch vessels.

8. A method for transvascularly delivering a medical device to a site of a cardiac valve of a patient, said method comprising:

introducing a first lumen into a vascular system;

navigating a distal end of said first lumen through said vascular system to an ostia of side branch vessels in an aortic arch;

expanding, from an orifice at said distal end of said first lumen, at least a portion of an expandable embolic protection filter, thereby covering said ostia of the side branch vessels in the aortic arch;

introducing a second lumen into said vascular system;

navigating a distal end of said second lumen through said vascular system to said site of said cardiac valve;

delivering said medical device through said second lumen to said site of said cardiac valve while said embolic protection filter covering said ostia.

* * * * *